United States Patent [19]

Sonenshine et al.

[11] Patent Number: 5,149,526
[45] Date of Patent: Sep. 22, 1992

[54] USE OF CHOLESTERYL ESTERS AS MOUNTING SEX PHEROMONES IN COMBINATION WITH 2,6-DICHLOROPHENOL AND PESTICIDES TO CONTROL POPULATIONS OF HARD TICKS

[75] Inventors: Daniel E. Sonenshine, Virginia Beach, Va.; J. Gordon Hamilton, Liverpool, England; William R. Lusby, Adelphi, Md.

[73] Assignee: The United States of America as represented by the Secretary of Agriculture, Washington, D.C.

[21] Appl. No.: 610,904

[22] Filed: Nov. 9, 1990

[51] Int. Cl.$^5$ .............................................. A01N 45/00
[52] U.S. Cl. ................................... 424/84; 514/182; 514/737; 514/171
[58] Field of Search ................ 514/182, 737, 171; 424/84

[56] References Cited

PUBLICATIONS

Hamilton, J. G. C. et al., "Cholestryl Oleate: Mounting Sexpheromone . . . " J. Insect. Physiol. vol. 35(11), 1989, pp. 873-879.
Hamilton et al., J. Chem. Ecol., vol. 14, No. 1 (1988), pp. 401-410.
Sonenshine et al., Exp. Appl. Acarol., vol. 1 (1985), pp. 23-34.
Sonenshine et al., J. Chem. Ecol., vol. 7, No. 2 (1981), pp. 345-357.
Ziv et al., J. Chem. Ecol., vol. 7, No. 5 (1981), pp. 829-840.

Primary Examiner—Allen J. Robinson
Assistant Examiner—John D. Pak
Attorney, Agent, or Firm—M. Howard Silverstein; John D. Fado; Janelle Graeter

[57] ABSTRACT

Compositions, methods and apparatus provide for the control of Ixodid hard tick populations. The compositions comprise a cholesteryl ester and 2,6-dichlorophenol. In combination, these compounds attract and induce mating behavior in male ticks thus disrupting normal mating, with subsequent reduction in tick populations.

6 Claims, 1 Drawing Sheet

USE OF CHOLESTERYL ESTERS AS MOUNTING SEX PHEROMONES IN COMBINATION WITH 2,6-DICHLOROPHENOL AND PESTICIDES TO CONTROL POPULATIONS OF HARD TICKS

BACKGROUND OF THE INVENTION

1 Field of the Invention

This invention relates to compositions including sterols and their esters, particularly, cholesteryl esters, a 2,6-dihalogenated-phenol and one or more pesticides. These compositions have utility in the management of ticks. The compositions are used to attract, trap and/or kill these pests.

2 Description of the Prior Art

Ticks transmit a greater variety of infectious diseases than any other group of hematophagous anthropods. Ticks along cause a $270 million loss per year to the U.S. cattle industry. For this reason there is interest in controlling and/or eradicating these pests.

As with insects, tick mating is regulated primarily by sex pheromones. Phenolic compounds such as 2,6-dichlorophenol (2,6-DCP) have been found in at least 14 species of ixodid ticks. These pheromones are secreted by sexually mature females in order to attract males [Sonenshine, D. E., Annu. Rev. Entomol., Vol. 30, (1985), pp. 1-28].

Female tick decoys have been made which incorporate 2,6-DCP and a toxicant into a device to lure and kill male ticks "U.S. Pat. No. 4,884,361, issued Dec. 5, 1988].

There is a major disadvantage inherent when using these prior art compositions in controlling ticks. While male ticks recognize phenolic compounds such as 2,6-dichlorophenol and 2,6-dibromophenol, (2,6-DBP) [Sonenshine, et al., J. Chem. Ecol., Vol. 2, No. 2, (1976), pp. 201-209] this recognition does not guarantee mating [Hamilton, et al., J. Chem. Ecol., Vol. 14, No. 1, (1988), pp. 401-410; Sonenshine, et al., Exp. Parasite. Vol. 54, (1982), pp. 317-330]. Male ticks attracted to 2,6-DCP applied to inanimate objects leave the objects without mating thus failing to recognize a potential mate.

It has been found that male ticks (*Dermacentor variabilis* and *Dermacentor andersoni*) exhibit probing and mounting behavior when exposed to hexane extracts of female tick cuticle [Hamilton, et al., J. Chem. Ecol., Vol. 14, No. 1, (1988). pp. 401-410]. Apparently, the cuticular lipids act as a mounting sex pheromone (MSP) to initiating mounting and copulation by the male.

It can be seen that there is a need for compositions and methods for their use that will lure male ticks and subsequently keep them in a vicinity for a sufficient time to kill them or alteratively, interrupt their mating cycle.

SUMMARY OF THE INVENTION

It is therefore an object of the present invention to provide compositions, comprising sterol esters and halogenated-phenols, ford their use in combination with toxicants to control populations of hard ticks. Particularly, a composition of a cholesteryl ester, 2,6-dichlorophenol and a pesticide is used to control, disrupt the mating cycle and/or kill male ticks. The composition may be applied to articles of manufacture for attracting and destroying ticks such as female tick decoys, traps or formulated into natural synthetic polymer resins for easy handling and distribution.

DETAILED DESCRIPTION OF THE INVENTION

Figure 1:
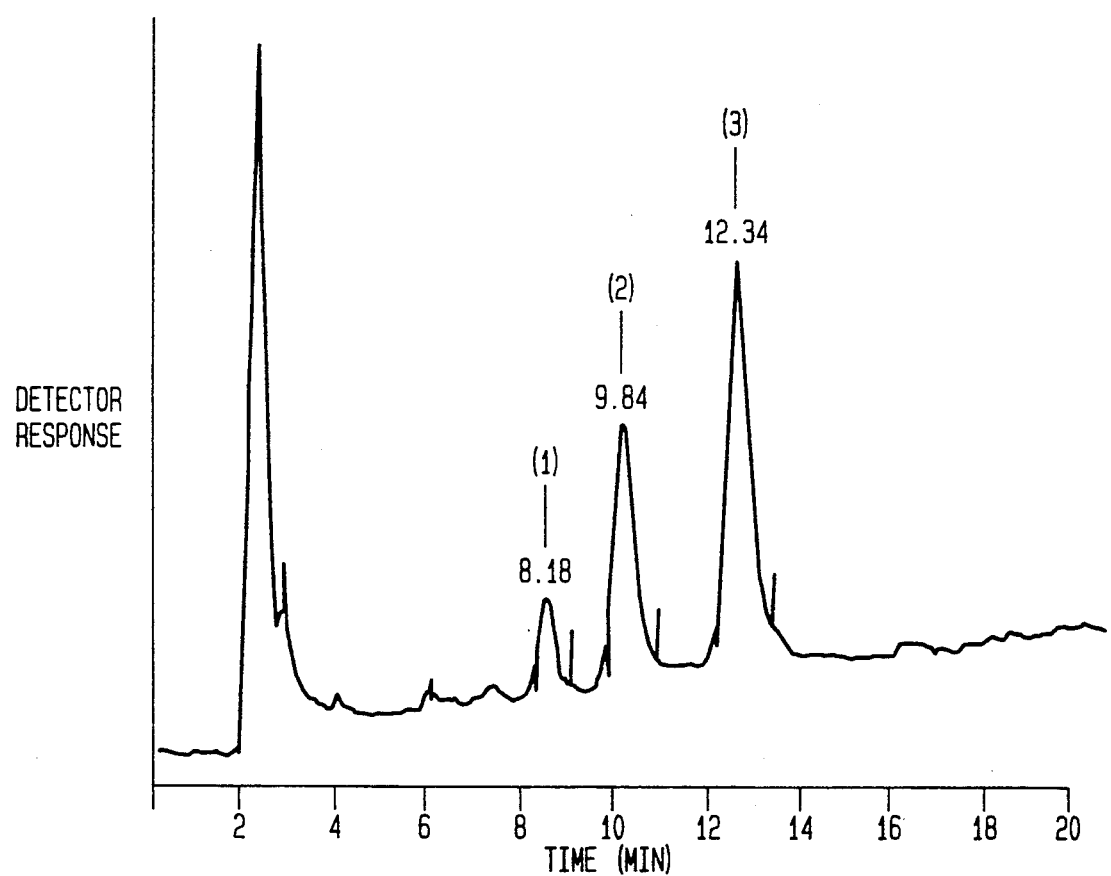
FIG. 1—High pressure liquid chromatogram illustrating the peaks detected when a sample of the BioSil A column purified *D. variabilis* female tick extract representing 1 female equivalent was injected into the HPLC. (1)=cholesteryl linolenate; (2)=cholesteryl linoleate; (3)=cholesteryl oleate.

Isolation and Identification of a Mounting Sex Pheromone

Materials and Methods

Ticks:

The American dog tick, *D. variabilis*, was colonized from wild-caught ticks collected near Richmond, Va. The Rocky Mountain wood tick, *D. andersoni*, was colonized from a population obtained from the U.S. Public Health Service, Rocky Mountain Laboratory, Hamilton, Mont. Lone star ticks, *Amblyomma americanum*, were colonized from specimens collected in Suffolk, Va. Gulf coast ticks, *Amblyomma maculatum*, were colonized from specimens obtained from the livestock Insects Laboratory, U.S.D.A. Kerrville, Tex. Camel ticks, *Hyalomma dromedarii*, were colonized from specimens obtained from the U.S. Navy, U.S. NAMRU-3, Cairo, Egypt. Ticks were reared and incubated as described previously. [Sonenshine, et al, J. Chem. Ecol., Vol. 3, (1977), pp 695-706; Sonenshine, et al., J. Med. Ent., Vol 23, (1986), pp. 630-650]

Solvents, standards and support media:

Hexane, diethyl ether and methanol were capillary GC-MS grade; isopropanol and chloroform were HPLC grade (Burdick and Jackson, Inc., Muskegan, Mich.) The ether was redistilled to remove peroxides and other contaminants. HPLC grade acetonitrile was from Mallinckrodt (Paris, Ky.). 2,6-dichlorophenol (99% pure) was form Aldrich Chemical Company (Milwaukee, Wis.). Cholesteryl oleate (99% pure), cholesteryl linoleate (98% pure), cholesteryl linolenate (99% pure), hydrocarbons, fatty acids, alcohols, sterols and non-polar lipid mix were from Sigma Chemical Co. St. Louis, Mont.) (for details, see Table 2). Bio-Sil (Silicic Acid) 100-200 Mesh, was from BioRad Laboratories, Richmond, Calif.

Preparation of tick extracts:

Females of all species were allowed to feed on immunologically naive (i.e. never previously exposed to ticks) laboratory rabbits, *Oryctalagus cuniculus*, and removed from these hosts 7 days after attachment. Fed females (2000) were immersed in about 10 ml cold hexane (0°-4° C.) for 2-3 h. The hexane was decanted into a precleaned acid-washed beaker and the ticks washed 2 times with additional hexane, 30 min/wash. The hexane washes were combined, concentrated with a rotary evaporator, concentrated further with nitrogen to about 1 ml and stored at −20° C. until required for assay.

To determine the amounts of steryl esters present in unfed and fed virgin female *D. variabilis*, samples of 100 unfed females and 100 fed virgin females were immersed in 10 ml chloroform methanol (2:1, v/v) for 12 h. The solvent was decanted, the extraction repeated twice, the aliquots combined and concentrated (nitrogen). Following centrifugation, aliquots of the extract were assayed by thin-layer chromatography Bioassays:

Bioassays were performed as described by Hamilton and Sonenshine, J. Chem. Ecol., Vol. 14, (1988), pp. 401-410, and incorporated herein by reference.

Tests were done with sexually active males exposed to (1) cleaned females, i.e. delipidized by immersion in hexane (24-48 h); success of the cleaning was determined by observing loss of their ability to stimulate the characteristic male mounting response; and (2) extract-treated females, i.e. cleaned females onto which the extract was deposited. Controls were females from the same population fed on the same hosts, but not subjected to any of these treatments. Males were fed on separate rabbits and evaluated for sexual activity prior to their use in the bioassay. Each treated or control female (i.e. cleaned but not treated) was tested with 20 males, and each male was allowed up to 3 opportunities to respond. Scoring of the assay results was as described previously (Hamilton and Sonenshine, 1988, supra).

Tests were also done with males of the 5 different species to determine interspecific characteristics, if any, of the mounting sec pheromone. Males were exposed to cleaned females of each species, each female treated with its conspecific, purified (mounting sex pheromone) extract.

Chemical identification:

(1) Partition and fractionation. All glasswares were acid cleaned and dried prior to use. For a liquid:liquid separation, equal volumes of hexane and methanol were placed in a separating funnel, the crude hexane extract added, and the contents shaken vigorously for 5-10 min. Following separation, the 2 layers were collected. The methanol aliquot was transferred to a second separating funnel, an equal amount of hexane added, and the process repeated. Following separation, aliquots of the same solvent were combined, concentrated as described above, and tested for biological activity. For the acid/base/neutrals separation, the active fraction was separated into neutrals, weak acids, phenolics, etc., and basic molecules. Following separation, the 3 fractions were tested for biological activity.

Fractionation of neutrals in the tick extract was done on a BioSil A column. Column parameters were: (1) weight of silica to extract, 40:1; (2) column length vs diameter, 9:1; (3) solvent flow rate, 2 ml/min. Following cleaning with hexane and hexane:diethyl ether, samples of n-octacosane, 1-octodecane, docosanoic acid, and tetracosanol were used as standards and the solvent ratios adjusted for optimal elution of each compound. After standardizing the column, a sample of the neutral fraction of the tick extract containing 2000 female equivalents was loaded onto the column and eluted with 5 ml aliquots (3 times) of hexane and hexane:diethyl ether (v/v) in the following ratios: 99:1; 98:2; 95:5; 90:10; and 80:20. Thin-layer chromatography (see below) was used to monitor complete elution of removable material with each solvent system. Following the last aliquot, the silica gel was removed and extracted in a Soxhlet extractor with hexane. All fractions were concentrated (nitrogen), and monitored for biological activity by bioassay. Bioassays were performed at concentrations of 1 and 10 female equivalents of each fraction.

(2) Thin layer Chromatography (TLC) was done to characterize the extracts from the different species, and monitor the progress of the fractionation of the $D.$ $variabilis$ extract. Support media were Baker-Flex $1B_2$ plates (20×20 cm) (J. T. Baker Chemical Co., Phillipsbury, N.J.) and High Performance TLC plates (HPTLC) (Whatman Chemical Sepration. Inc. Clifton, N.J.). TLC plates were cleaned twice in hexane and twice in the solvent used for analysis. Solvent systems were: ($1a$) for the $1B_2$ paltes, isopropyl ether:acetic acid (96:4 v/v) followed by petroleum ether:diethyl ether:acetic acid (90:10:1, v/v); (1b) for the chloroform:methanol extracts, hexane:diethyl ether:acetic acid (80:20:1); (2) for the TLC plates, hexane followed by hexane:diethyl ether (80:20, v/v). Crude extracts of all 5 tick species were assayed. Lipid spots were visualized by spraying with 50% sulphuric acid and heating to 100° C.

The steryl esters in the unfed and fed female tick extracts were quantitated using a Kontes Fiber Optics thin layer scanner (Kontes, Vineland, N.J.) and Hewlett Packard Integrator (Hewlett Packard, Downer's Grove, 111.) Comparisons were made with serial dilutions of authentic cholesteryl oleate.

(3) High Pressure Liquid Chromatography (HPLC). This was done with the fraction eluted from the BioSil A column showing the highest biological activity. Analysis was done with a Waters HPLC system comprising a model 721 systems controller, 730 data module, paired model 510 pumps, U6K injector and a model 441 Ultraviolet fixed wavelength (214 nm) absorbance detector (Waters, Milford, Mass.) using a 25 cm Whatman Partasil 5-ODS-3 reversed phase analytical column (Whatman, Hillsboro, Ore.) The solvent was acetonitrile:isopropanol (60:40) (isocratic) at 2 ml/min.

Standards included cholesteryl oleate, cholesteryl linoleate and cholesteryl linolenate. Fractions were collected manually. Co-elution of sample peaks and authentic standards was used for tentative identification.

(4) Coupled Gas Chromatography-Mass Spectrometry (GC-MS). samples for GC-MS were collected from the HPLC and presented as individual fractions. GC-MS was done on a MAT model 4510 instrument equipped with a direct exposure probe and fitted with a DB-1fused silica glass capillary column, 30 m×0.032 mm i.d., with a 0.25 um film (bonded dimethylsilicone) (J & W Scientific, Folson, Calif.). The purified tick sample peak and the authentic cholesteryl oleate standard were examined by direct exposure probe electron ionization mass spectrometry and chemical ionization spectrometry. Electron ionization spectra were collected at an indicated source temperature of 150° C. and an ionizing voltage of 70 eV. Chemical ionization spectra were obtained using methane, ammonia, perdeutero ammonia and $^{15}N$-ammonia as regent gases at an indicated source temperature of 60° C. Probe samples were desorbed from the probe tip loop by application of a heating current of 20 mA/s. GC-MS samples of methyl esters were injected at a helium carrier head pressure of 11 psi and a column temperature of 160° C.

To determine the identity of structural moieties of the mounting sex pheromone, the HPLC purified sample fractions were saponified. Approximately 10 ug of HPLC fraction 3 was saponified by refluxing with 4% methanolic potassium hydroxide at 65° C. for 4 h, extracted with hexane, and concentrated. The fatty acid products of the saponification were methylated with diazomethane. The resultant sterol moiety or moieties and fatty acid methyl esters ere analyzed by GC-MS (electron ionization). The same procedure was used with authentic cholesteryl oleate.

Statistical tests:

Duncan's Multiple Range test was used to evaluate differences in bioassay test results with different fractions of authentic compounds applied to the cleaned females. It was also used to compare male responses in the heterospecific assays.

Biological activity of the fractions:

Preliminary analysis of silica gel column fraction 3 by probe MS suggested the presence of a steryl ester. Table 2 summarizes the results of TLC assays for separation of the tick extracts into their component lipid classes.

TABLE 2

Results of thin-layer chromatographic separations of lipid extract (surface washes) from 5 species of hard ticks (Ixodidae)*

| Species | Hydrocarbons | Hydrocarbons | Steryl esters | Compounds classes and R values | | |
|---|---|---|---|---|---|---|
| | | | | FAMEs | Fatty acids | Cholesterol |
| D. variabilis | 0.99 | 0.97 | 0.84 | 0.70 | 0.65 | 0.37 |
| D. variabilis Fraction 3 | — | — | 0.84 | — | — | — |
| A. americanum | 0.99 | 0.96 | 0.84 | — | — | 0.37 |
| A. maculatum | — | — | 0.84 | 0.74 | 0.65 | 0.37 |
| H. dromedarii | 0.99 | 0.97 | 0.84 | — | 0.65 | 0.37 |
| Steryl ester[1] | — | — | — | — | — | — |
| Cholesterol | — | — | — | — | — | 0.37 |
| Hydrocarbon[2] | 0.99 | — | — | — | — | — |
| NPLM[3] | — | — | 0.85 | — | 0.65 | 0.37 |
| Lipid standards[4] | — | — | — | 0.74 | — | — |
| Fatty acids | — | — | — | — | 0.64 | — |

*Abbreviations: FAMEs = fatty acids methyl esters; NPLM, non-polar lipid mix; R = ratio position of observed to position of solvent front in centimeters.
Most intensely charring spots are shown in bold face.
Fraction eluted from silica gel column in hexane:diethyl ether, 99:1 (see text for details).
[1]Cholesteryl oleate, 50 ug.
[2]Hydrocarbons were n-tetradecane and n-tetradecane (each 70 ug).
[3]NPLM = non-polar lipid mix, including cholesteryl oleate, methyl oleate, triolein, oleic acid and cholesterol (each 70 ug).
[4]Fatty acid methyl esters (FAMEs): a mixture including methyl esters of linoleic, linolenic, palmitic and stearic acids (each 70 ug).

Following the hexane:methanol partition, virtually all of the biological activity (89%) was found in the hexane layer. When the activity fraction was separated further by the acid/base/neutral extraction, virtually all of the biological activity (91%) was found in the neutral fraction. When a sample containing 10 female-equivalents of this fraction was separated by column chromatography, no significant biological activity was found in the hexane eluate (F2), the fraction in which hydrocarbons were expected to elute. However, biological activity was found in several of the hexane:diethyl ether eluates (F3, 6 and 7). The highest activity was found in the third or 99:1 hexane:diethyl ether eluate, hereafter termed fraction 3. When a sample of this extract continuing 1 female equivalent was separated, biological activity was found only in the 99:1 hexane:diethyl ether eluate (F3). In contrast, biological activity was lost in all other fractions (Table 1). These findings suggested that a compound or class of compounds slightly more polar than hydrocarbons was responsible for the biological activity.

TABLE 1

Results of bioassays with fractions eluted from the BioSil A silica column. Male responses are given in percent (%).

| | Concentration of elute in female equivalents | |
|---|---|---|
| Eluate | 1 | 10 |
| F1 Column blank | 4 | 4* |
| F2 H | 6* | 5* |
| F3 H:De (99:1) | 83 | 81 |
| F4 H:De (99:2) | 11* | 21* |
| F5 H:De (99:5) | 7* | 21* |
| F6 H:De (99:10) | 5* | 34 |
| F7 H:De (80:20) | 0* | 44 |
| F8 H:De column extract (soxhlet) | 11* | 31 |

*Not significantly different from each other (P < 0.01).
These values are significantly greater than those indicated by *, but not from each other (P < 0.01).
These values are significantly greater than all others, but not from each other (P < 0.01).
H = hexane; De = diethyl ether.

Chemical characterization of the extracts:

Spots observed with the crude extracts from all 5 species were compared with the authentic standards or standard mixtures. All tick extracts had abundant material corresponding to steryl esters, fatty acids and cholesterol. All but A. maculatum had trace of substances that co-chromatographed with hydrocarbons and all but A. americanum had material that co-chromatographed with triacyl glycerols and fatty acid methyl esters. TLC of silica gel column fraction 3 showed only a single spot which co-chromatographed with steryl esters. These findings show that the mounting sex pheromone consisted of a steryl ester or a blend of different steryl esters. They also indicate that this class of compounds is widespread in tick cuticle lipids.

Feeding led to a marked increase in steryl ester content. In D. variabilis, this class of compound increased from 4.4 μg/unfed female of 38.6±2.6 μg/fed virgin female.

Chemical characterization of the active fraction:

HPLC of silica gel column fraction 3 revealed 3 major peaks. When compared by co-injection and co-elution with authentic standards, these peaks were identified as (1) cholesteryl linolenate, (2) cholesteryl linoleate and (3) cholesteryl oleate (FIG. 1). A 1 female equivalent aliquot was found to contain 0.16 μg of (1), 4.23 μg of (2) and 12.1 μg of (3). Bioassay of peaks (2) and (3) revealed strong biological activity; peak (1) was unstable and could not be assayed. Aliquots collected before, between or after elution of the utra-violet-visible peaks were not active.

Chemical identification of the active fraction:

The peak co-eluting with cholesteryl oleate was collected and analyzed by desorption chemical ionization and electron ionization mass spectrometry. Desorption chemical ionization mass spectral analysis of biologically active HPLC peak 3 using ammonia as the reagent gas yielded a presumed ammonium adduction at m/z 668 [100%, $(M+NH_4)^+$]. An analogous examination using $^{15}NH_3$, provided a base peak at m/z [100%, $(M+^{15}NH_4)^+$] and demonstrated the absence of exchangeable hydrogen. Analysis of the sample by electron ionization produced a spectrum characterized by a base peak at m/z 368 and numerous less abundant fragmentations (Table 3) consisted with cholesteryl oleate.

TABLE 3

Mass spectrometric data from analysis of the *D. varibilis* biological active fraction purified by HPLC.

HPLC fraction co-eluting with cholesteryl oleate
$NH_3$—Cl—MS m/z: 668 [100% $(M + NH_4)^+$].
$^{15}NH_3$—Cl—MS m/z: 669 [100% $(M + ^{15}NH_4)^+$].
$CH_4$—Cl—MS m/z: 651 [6%, 9M + H)$^+$], 649[9, (M + H)$^+$], 369 [100, (M + H-282$^+$].
$ND_3$—Cl—MS m/z: 672 [100%. M + $ND_4)^+$].
EI—MS m/z: 368(100%), 353(8). 260(7). 255(6), 247(7), 147(11), 95(10), 83(10), 81(11), 71(10), 69(13), 57(22), 55(15).

Sponification products
Cholesterol: EI—MS m/z: 386(100%), 371(25), 368(24), 353(26), 301(55), 275(60), 255(25), 231(39)159(45), 133(48), 119(48), 207(75), 105(76), 81(69), 69(41), 55(73).
Cholestanol: EI—MS m/z: 388(55%), 373(6), 355(8), 234(59), (233(93, 215(100), 165(36), 147(22), 108(68), 81(84), 79(24), 69(33), 57(47), 55(76).
Methyl oleate: EI—MS m/z: 269(4%), 264(28), 222(13), 180(9), 123(14). 110(21), 97(48), 83(49). 74(53), 69(58), 55(100).

All of the above chemical ionization spectra as well as the electron ionization spectrum were identified to the corresponding analysis for cholesteryl oleate.

The sterol fraction resulting from saponification of HPLC peak No. 3 contained a major (approx. 90%) component and a minor (approx. 10%) component, CG-MS (electron ionization) analysis and GC retention time analysis identified these sterol components as cholesterol and cholestanol respectively. Analysis of the resultant fatty acid moiety (after methyl esterification) by GC-MS (electron ionization) confirmed the presence of oleic acid (Table 3). The double bond geometry as confirmed as trans by comparison of methyl oleate (tarns) and methyl elaidate (cis) GC retention times with that of the authentic fatty acid methyl esters not shown in the table.

These results indicate that cholesteryl oleate was dominant component of the HPLC fraction 3 (90%); cholestanyl oleate was a minor component of this peak.

Bioassay responses to steryl esters:

Table 4 summarizes responses by *D. variabilis* males to different steryl as compared to the natural extract (mounting sex pheromone).

TABLE 4

Responses of male tick (%) to females treated with steryl ester, cholesterol and mounting sex pheromone*

| | Concentration per cleaned female (ug) | | | | |
|---|---|---|---|---|---|
| | 10 | 2.5 | 1 | 0.5 | 0.1 |
| Cholesteryl oleate (C18:1) | 92 | 78 | 81 | 36 | 18 |
| Cholesteryl linoleate (C18:2) | 67 | 63 | 63 | 57 | 27 |
| Cholesteryl linolenate (C18:3) | 71 | 64 | 46 | 53 | 33 |
| Cholesteryl stearate (C18:0) | 58 | 53 | 50 | 35 | 16 |
| Cholesteryl arachidate (C20:0) | 66 | 65 | 56 | 50 | 34 |
| Cholesteryl palmitate (C16:0) | 52 | 56 | 28 | 16 | 7 |
| Cholesteryl laurate (C12:0) | 70 | 64 | 65 | 51 | 20 |
| Cholesteryl acetate (C2:0) | 48 | 40 | 41 | 13 | 7 |
| Cholesteryl | 0 | ND | ND | ND | ND |
| Hexane | 14 | 0 | 2 | 0 | 0 |
| Mounting sex pherome | 100 | ND | 95 | ND | 40 |

*Females were cleaned by immersion in hexane for 48 h; standards or mounting sex peromone and 2,6-dichlorophenol (10 ng) dissolved in hexane were pipetted onto the cleaned females. Following solvent evaporation (5-10 min), behavioural assays were done with fed males. Each female was assayed with 20 males, with 3 trials/male, as described by Hamilton and Sonenshine (1988); values in the body of the table represent the mean % positive response; ND = not done. Not significantly different from mounting sex pheromone (P > 0.05) by Duncan's Multiple Range test. Significantly different from mounting sex pheromone (P < 0.01) by Duncan's Multiple Range test.

The response to 10 and 1 µg of cholesteryl oleate, amounts comparable to about 1 and 0.1 female equivalent, is not significantly different (Duncan's Multiple Range test, P<0.05) from that observed with the natural pheromone at 10 and 1 female equivalents and accounts for all of the observed behaviour Significantly lower responses were obtained with the other steryl esters; at 1 µg, the responses to all of the other steryl esters were significantly different (lower) by this test from mounting sex pheromone.

Bioassay responses of males of five different species to tick extracts:

Table 5 summarizes the results of test using males of 5 different species to conspecific and heterospecific crude extracts. *D. variabilis* males did not distinguish between *D. variabilis* and *D. andersoni* extracts, but they showed much weaker or insignificant responses to extracts of other genera. *D. andersoni* males, however, responded strongly to extracts of all species. *A. americanum* and *A. maculatum* males responded more strongly to extracts of the same genus than to those of the other genera.

TABLE 5

Bioassay responses of male ticks of 5 different species of Ixodidae to cleaned females treated with crude extract from these same females*.

| Tick species ( ) | MSP concentration FE | D. variabilis | D. andersoni | A. americanum | A. maculatum |
|---|---|---|---|---|---|
| D. vaiabilis | 1.0 | 90 | 47 | 31 | 43 |
| | 0.1 | 80 | 43 | 29 | 23 |
| | 0.01 | 3 | 23 | 0 | 3 |
| D. andersoni | 1.0 | 84 | 54 | 5 | 6 |
| | 0.1 | — | 20 | 18 | 4 |
| | 0.01 | — | 19 | 0 | 0 |
| A. americanum | 1.0 | 29 | 58 | 80 | — |
| | 0.1 | 25 | 40 | 84 | 46 |
| | 0.01 | 6 | 3 | 19 | — |
| A. maculatum | 1.0 | 41 | 72 | 54 | 71 |
| | 0.1 | 23 | 43 | 39 | 79 |

TABLE 5-continued

Bioassay responses of male ticks of 5 different species of Ixodidae to cleaned females treated with crude extract from these same females*.

| Tick species ( ) | MSP concentration FE | D. variabilis | D. andersoni | A. americanum | A. maculatum |
|---|---|---|---|---|---|
| | 0.01 | 8 | 58 | 15 | 34 |

Females were cleaned by immersion in hexane for 48 h; the tick extract fracation co-eluting with steryl standards was collected and diluted to the dilutions shown in the table. Samples of each were applied to cleaned conspecific females. Following solvent evaporation (5-10 min), behavioural assays were done with sexually active males (each treated female with 5 males, 3 trails/male). The values in the table represent the mean percent response. $^{a,b,c}$Male response (%) of each of the 4 species were compared with each other for each species of female extract at a given concentration in the same row. Responses with the same superscript were not significantly different from one another by Duncan's Multiple Range test. Male responses (%) of a given species were compared with each other for each of the 4 species of female extracts at a given concentration in the same column. Responses with the same superscript were not significantly different from one another by Ducan's Multiple Range test.
MSP = mounting sex pheromone; FE = female equivalent.

EXPERIMENTAL PROCEDURES

Conspecific Tests on Rabbits

To test effectiveness of decoys containing both pesticide and the two pheromones in killing male ticks, the decoys were attached to the bodies of shaved, tranquilized rabbits (Acerpromazine, Aveco, Fort Dodge, Iowa). The term decoy in the context of the present invention is understood to mean, those articles of manufacture intended for destroying arthropods that bear resemblance to the arthropod of interest, such as described but not limited to those disclosed in U.S. Pat. No. 4,884,361. Each rabbit was infested with 5 living attached, partially fed D. variabilis females, distributed at random over the body of the animal. Decoy, 50/rabbit, were glued (rubber cement, Union Rubber and Asbesttos Co. Trenton, N.J.) randomly to the back and flanks of the tick infested rabbits so as to achieve a ratio of 10 decoys to one live female tick. Cardboard collars were installed around the neck of each rabbit to prevent the animal dislodging the decoys or the ticks. The experiment was replicated 10 times. Controls were performed with decoys containing 1) 2,6-DCP only, 2) 2,6-DCP and MSP and 3) 2,6-DCP and Propoxur (see Table 6). Alternatively, any pesticide or toxicant known in the art for the control of arthropod pests can be substituted such as permethrin, organophosphorus compounds and the like. Subsequently, the same 4 treatments were repeated but with a ratio of 5 decoys to one live female and the experiment replicated 5 times (see Table 7).

TABLE 6

Ability of pheromone-pesticide treated plastic decoys to kill male ticks, D. variabilis, and prevent mating when administered at a ratio of 10:1, decoys to live female ticks. All values are percentages of numbers of males released.

| | TREATMENT 1 Both pheromones + Propoxur Hrs > males released | | | TREATMENT 2 Both pheromones only Hrs > males released | | | TREATMENT 3 2,6-DCP + Propoxur Hrs > males released | | | TREATMENT 4 2,6-DCp only Hrs > males released | | |
|---|---|---|---|---|---|---|---|---|---|---|---|---|
| Location of males | 0.0 0.5 | — 24.0 | 48.0 | 0.0 0.5 | — 24.0 | 48.0 | 0.0 0.5 | — 24.0 | 48.0 | 0.0 0.5 | — 24.0 | 48.0 |
| Mating with decoys Attached | 89.0 ±3.3 | — | — | 73.0 ±4.8 | 11.4 ±0.7 | 14.6 ±1.2 | 20.0 ±4.0 | 0.0 | 0.0 | 23.0 ±5.8 | 6.5 ±0.3 | 10.0 ±0.7 |
| beside decoys Mating with | 11.0 +3.3 | — | — | 17.0 ±1.1 | 64.3 ±1.0 | 70.8 ±1.4 | 24.0 ±3.8 | 11.0 ±3.6 | 2.0 ±2.0 | 14.0 2.1 | 9.0 0.5 | 25.0 1.0 |
| live females Attached | 0.0 | — | — | 0.0 | 5.7 ±0.3 | 8.3 ±0.6 | 6.0 ±1.6 | 3.0 ±1.5 | 0.0 | 19.0 ±3.3 | 8.1 ±0.4 | 7.5 ±0.5 |
| elsewhere | 0.0 ±1.2 | — | — | 10.0 | 17.1 ±3.7 | 6.3 ±0.6 | 50.0 ±0.4 | 24.0 ±4.0 | 2.0 ±5.5 | 44.0 ±1.3 | 56.5 ±8.0 | 57.0 ±1.0 |
| Dead | 100.00 | — | — | 0.0 | 1.4 ±0.1 | 0.0 | 36.0 ±4.3 | 73.0 ±4.5 | 98.0 ±1.3 | | | |

*Males dead: two deposited spermatophores.
**Males attached dead.

TABLE 7

Ability of pheromone-pesticide treated plastic decoys to kill male ticks, D. variabilis, and prevent mating when administered at a ratio of 5:1, decoys to live female ticks. All values are percentages of numbers of males released.

| | TREATMENT 1 Both pheromones + Propoxur Hrs > males released | | | TREATMENT 2 Both pheromones only Hrs > males released | | | TREATMENT 3 2,6-DCP + Propoxur Hrs > males released | | | TREATMENT 4 2,6-DCp only Hrs > males released | | |
|---|---|---|---|---|---|---|---|---|---|---|---|---|
| Location of males | 0.0 0.5 | — 24.0 | 48.0 | 0.0 0.5 | — 24.0 | 48.0 | 0.0 0.5 | — 24.0 | 48.0 | 0.0 0.5 | — 24.0 | 48.0 |

TABLE 7-continued

Ability of pheromone-pesticide treated plastic decoys to kill male ticks. *D. variabilis*, and prevent mating when administered at a ratio of 5:1, decoys to live female ticks. All values are percentages of numbers of males released.

| | TREATMENT 1 Both pheromones + Propoxur Hrs > males released | | | TREATMENT 2 Both pheromones only Hrs > males released | | | TREATMENT 3 2,6-DCP + Propoxur Hrs > males released | | | TREATMENT 4 2,6-DCp only Hrs > males released | | |
|---|---|---|---|---|---|---|---|---|---|---|---|---|
| Mating with decoys | 66.0 ±11.5 | — | — | 72.0 ±5.2 | 3.1 ±2.3 | 2.3 ±1.5 | 26.0 ±9.6 | 8.0 ±7.2 | 6.0 ±5.4 | 26.0 ±8.3 | 0.0 | 2.2 ±1.9 |
| Attached beside decoys | 30.0 ±10.0 | 4.6 ±3.6 | — | 22.0 ±5.3 | 12.4 ±2.4 | 8.2 ±4.0 | 24.0 ±6.7 | 6.0 ±5.4 | 4.0 ±3.6 | 24.0 ±6.1 | 8.0 ±1.3 | 7.6 ±2.3 |
| Mating with live females | 4.0 ±3.6 | — | — | 6.0 ±2.2 | 0.4 ±0.4 | 1.8 ±1.6 | 6.0 ±3.6 | 2.0 ±1.8 | 4.0 ±2.2 | 32.0 ±7.7 | 5.0 ±1.4 | 3.6 ±1.7 |
| Attached elsewhere | 0.0 | — | — | 0.0 | 4.0 ±1.6 | 7.0 ±2.7 | 44.0 ±8.3 | 30.0 ±2.8 | 80.0 ±5.2 | 18.0 ±8.7 | 6.5 +0.9 | 6.5 ±1.6 |
| Dead | 96.0 ±3.6 | 4.0 ±3.6 | — | 0.0 | 0.0 | 0.0 | 40.0 ±11.3 | 78.0 ±4.4 | 98.0 ±1.8 | 0.0 | 0.0 | 0.0 |

Male American dog ticks fed previously on other rabbits were placed on the decoy treated animals. Fed males will search for and mate with female ticks when given an opportunity. To test the treatments, 10 fed male ticks were released onto the back of a treated animal and their movements observed and recorded continuously for 30 minutes.

The following observations made: 1) The number and duration of contacts of decoys and real females by male ticks. 2) The number of males which contacts the decoys or real females and attempted further mating behavior. 3) The number of males attaching and feeding beside decoys or real females. 4) Numbers of males attaching and feeding in areas between decoys and rear females. 5) Number of dead and dying males. Time until death of the male tick in contact with decoys, mating with live females, attached to the host, or dead. Observations were carried out in a walk-in environmental chamber (Temp 85°±3° F. and 80±5% RH).

EXPERIMENTAL PROCEDURES

Interspecific and Intergenric Tests

To determine whether the decoy would attract and kill male ticks of other species, males of the fur different tick species were tested against decoys coated with MSP (1 FE/decoy) made from female *D. variabilis* or *D. andersoni* as described above and attached to rabbits. Live female ticks were interspersed evenly among the decoys (ratio 1:5). Decoy types and males of each different species were tested separately and each experiment was repeated 2×.

EXPERIMENTAL PROCEDURES

Conspecific Tests on Livestock

The effectiveness of the decoys on Guernsey cattle was tested. Three young calves, each approximately 8 weeks old, and weighing approximately 200 lbs were used. The animals were washed with a non-insecticidal shampoo. A total of 30 pre-fed live female dog ticks, *D. variabilis*, were applied to each of the 3 animals at random. The ticks were distributed over the neck, flanks, back, and rump on both sides of the body and allowed to reattach. Twenty-four hours later, decoys impregnated with pheromone and pesticide were attached to the test animals at a ratio of 10:1, decoys to live females and coated with MSP extract. Decoys impregnated with pheromone only were dispersed on a third animal, which served as the control. Following dispersal of the decoys, 60 fed male ticks, were released onto each of the 3 test animals. Unlike the previous tests when the male responses were recorded continuously for the first 0.5 hrs, the distribution of the male ticks and their status, living or dead, was recorded only at 0.5 hrs and 1.5 hrs. The test was replicated 10 times.

FORMULATIONS AND ADMINISTRATION

The application of a composition including a cholesteryl ester particularly cholesteryl oleate and 2,6-DCP to an animal alone or in a device selected to dissipate the 2,6-DCP as a long range attractant, e.g., microcapsules, plastic decoys or a trap using a rubber septum, hollow fibers, capillary filaments, polyethylene or gelatin capsules, multilayer tapes made of natural or synthetic polymer resins. PVC dispenser, silicon tubing, confuse male attempts to mate with female ticks. The addition of one or more pesticides or toxicants incorporated into the afore mentioned materials, kill the males resulting in unmated females. Since unmated females are unable to produce fertile eggs, subsequent tick populations are thereby reduced.

It can be seen there are many variations and alternatives that may be practiced by the disclosure of the present invention. It is intended that the spirit and scope of this invention include all such variations and alternatives as illustrated by the appended claims.

We claim:

1. A tick attractant composition consisting essentially of:
   a) a cholesteryl ester, wherein the ester s an ester of 2 to 22 carbons in length, and
   b a 2,6-dihalogenated phenol, selected from the group consisting of 2,6-dichlorophenol and 2,6-dibromophenol,
   in an amount and proportion effective for attracting ticks.

2. The composition of claim 1, wherein the cholesteryl ester is cholesteryl oleate.

3. The composition of claim 1, wherein the 2,6-dihalogenated phenol is 2,6-dichlorophenol.

4. The composition of claim 1, wherein the 2,6-dihalogenated phenol is 2,6-dibromophenol.

5. The composition of claim 1, wherein the cholesteryl ester is cholesteryl oleate and the 2,6-dihalogenated phenol is 2,6-dichlorophenol.

6. A method for attracting male ticks comprising administering to a predetermined surface an effective amount of a composition comprising:
 i) a cholesteryl ester, wherein the ester is an ester of 2 to 22 carbons in length, and
 ii) a 2,6-halogenated phenol selected from the group consisting of 2,6-dichlorophenol and 2,6-dibromophenol,
said amount being effective for attracting male ticks.

* * * * *